United States Patent
Hendriks et al.

(10) Patent No.: US 11,051,698 B2
(45) Date of Patent: Jul. 6, 2021

(54) OPTICAL MICROSCOPY PROBE FOR SCANNING MICROSCOPY OF AN ASSOCIATED OBJECT

(71) Applicant: KONINKLIJKE PHILIPS N.V., Eindhoven (NL)

(72) Inventors: Bernardus Hendrikus Wilhelmus Hendriks, Eindhoven (NL); Waltherus Cornelis Bierhoff, Veldhoven (NL); Nenad Mihajlovic, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 283 days.

(21) Appl. No.: 14/356,931

(22) PCT Filed: Oct. 31, 2012

(86) PCT No.: PCT/IB2012/056039
§ 371 (c)(1),
(2) Date: May 8, 2014

(87) PCT Pub. No.: WO2013/072796
PCT Pub. Date: May 23, 2013

(65) Prior Publication Data
US 2014/0316282 A1    Oct. 23, 2014

Related U.S. Application Data

(60) Provisional application No. 61/559,179, filed on Nov. 14, 2011.

(51) Int. Cl.
*G02B 21/00*     (2006.01)
*A61B 5/00*      (2006.01)
(Continued)

(52) U.S. Cl.
CPC ........ *A61B 5/0084* (2013.01); *A61B 1/00096* (2013.01); *A61B 1/00177* (2013.01);
(Continued)

(58) Field of Classification Search
CPC ... A61B 5/0075; A61B 5/0066; A61B 5/0084; A61B 5/0062; A61B 5/6852;
(Continued)

(56) References Cited

U.S. PATENT DOCUMENTS 3,901,220 A * 8/1975 Koyasu .............. A61B 1/00165
                                                   600/176
4,905,082 A    2/1990 Nishigaki et al.
(Continued)

FOREIGN PATENT DOCUMENTS

DE     102006046554     4/2008
EP        1683472       7/2006
(Continued)

OTHER PUBLICATIONS

B.H. Hendriks, et al., "High-Resolution Resonant and Nonresonant Fiber-Scanning Confocal Microscope", Journal of Biomedical Optics 16(2), Feb. 2011, pp. 026007-1 through 026007-8.

*Primary Examiner* — James M Kish

(57) ABSTRACT

An optical microscopy probe for scanning microscopy imaging of object has a housing with an optical window at a side position at the distal end of the housing, and an optical guide having an objective lens rigidly coupled to an end portion of the optical guide. The optical guide is displaceably mounted in a transverse direction of the housing so as to enable optical scanning in a region of interest. A relay lens unit is rigidly mounted at the distal end of the probe and it has a first lens, a second lens and a mirror. The relay lens unit is optically arranged relative to the objective lens for allowing
(Continued)

scanning microscopy through the optical window at the side of the distal end of the housing.

19 Claims, 13 Drawing Sheets

(51) Int. Cl.
  *A61B 1/00* (2006.01)
  *G02B 23/26* (2006.01)
  *G02B 23/24* (2006.01)
  *G02B 26/10* (2006.01)
  *G02B 23/06* (2006.01)
(52) U.S. Cl.
  CPC ...... *A61B 1/00179* (2013.01); *G02B 21/0028* (2013.01); *G02B 21/0036* (2013.01); *G02B 23/2423* (2013.01); *G02B 23/26* (2013.01); *G02B 26/103* (2013.01); *A61B 1/00165* (2013.01); *G02B 23/06* (2013.01); *G02B 23/2446* (2013.01)
(58) Field of Classification Search
  CPC .............. A61B 5/0068; A61B 1/00172; A61B 1/00096; A61B 1/07; A61B 3/102; A61B 1/00117; A61B 1/00165; A61B 1/00174–00183; A61B 1/00163–0017; G02B 23/2446; G02B 23/2423; G02B 23/06; G02B 23/26; G02B 21/0036; G02B 26/103
  See application file for complete search history.

(56) References Cited

U.S. PATENT DOCUMENTS

| | | | | |
|---|---|---|---|---|
| 5,045,936 A * | 9/1991 | Lobb | ..................... | A61B 1/0008 348/135 |
| 5,445,142 A * | 8/1995 | Hassler, Jr. | ......... | A61B 1/00087 600/105 |
| 5,865,725 A * | 2/1999 | Arai | ................... | A61B 1/00177 600/169 |
| 6,485,413 B1 * | 11/2002 | Boppart | ............. | A61B 1/00096 356/450 |
| 6,564,087 B1 * | 5/2003 | Pitris | ................... | A61B 1/00172 600/478 |
| 7,463,396 B2 | 12/2008 | Lauer | | |
| 7,559,891 B2 * | 7/2009 | Farr | ....................... | A61B 1/055 600/166 |
| 7,716,970 B2 | 5/2010 | Watanabe et al. | | |
| 7,999,945 B2 * | 8/2011 | Zara | ..................... | A61B 5/0066 356/479 |
| 9,039,609 B2 * | 5/2015 | Farr | ..................... | G02B 25/001 359/462 |
| 2004/0017961 A1 * | 1/2004 | Petersen | .............. | A61B 5/0066 385/12 |
| 2004/0076390 A1 * | 4/2004 | Dong Yang | ......... | A61B 1/00096 385/116 |
| 2006/0052708 A1 * | 3/2006 | Iddan | ................... | A61B 1/0005 600/476 |
| 2007/0238955 A1 * | 10/2007 | Tearney | ............. | A61B 1/00096 600/407 |
| 2008/0221388 A1 * | 9/2008 | Seibel | ................ | A61B 1/00177 600/109 |
| 2009/0026888 A1 * | 1/2009 | Melville | ............ | A61B 1/00172 310/335 |
| 2009/0262361 A1 | 10/2009 | Tanioka et al. | | |
| 2009/0270683 A1 | 10/2009 | Farr et al. | | |
| 2011/0019255 A1 * | 1/2011 | Murayama | ........... | G02B 23/243 359/209.1 |
| 2011/0134521 A1 * | 6/2011 | Truong | .............. | G01N 21/6408 359/388 |
| 2011/0178409 A1 * | 7/2011 | Harris | ................... | A61B 5/0066 600/476 |
| 2012/0101374 A1 * | 4/2012 | Tearney | ............... | A61B 5/0066 600/427 |
| 2014/0316282 A1 | 10/2014 | Hendriks et al. | | |
| 2019/0200867 A1 * | 7/2019 | Yokota | ................. | G02B 26/103 |

FOREIGN PATENT DOCUMENTS

| | | |
|---|---|---|
| JP | H0387804 A | 4/1991 |
| JP | 2001515382 A | 9/2001 |
| JP | 2011099963 A | 5/2011 |
| WO | WO199838907 | 9/1998 |

* cited by examiner

OPTICAL MICROSCOPY PROBE FOR SCANNING MICROSCOPY OF AN ASSOCIATED OBJECT

CROSS-REFERENCE TO PRIOR APPLICATIONS

This application is the U.S. National Phase application under 35 U.S.C. § 371 of International Application Serial No. PCT/IB2012/056039, filed on Oct. 31, 2012, which claims the benefit of U.S. Application Ser. No. 61/559,179, filed on Nov. 14, 2011. These applications are hereby incorporated by reference herein.

FIELD OF THE INVENTION

The present invention relates to an optical microscopy probe for scanning microscopy imaging of an associated object, the probe being particular suited for medical examination of a patient. The present invention also relates to a corresponding optical microscopy system comprising an optical microscopy probe. The invention also relates to a corresponding method for performing scanning microscopy imaging.

BACKGROUND OF THE INVENTION

Microscopic imaging of living tissue in vivo could allow for real-time disease diagnosis, which could be very relevant for many medical applications. Various approaches have been investigated to develop miniature microscopes that are compatible with minimally invasive procedures. Most of these approaches involve either single-fibers or fiber-bundles to transmit and receive light. Important design criteria are the spatial resolution, the field of view (FOV), as well as the contrast that can be achieved.

Designs based on coherent fiber bundles have many advantages including the potential for high levels of miniaturization and mechanical flexibility, but are limited in resolution by the diameter and spacing of the fibers. With some designs, Fresnel reflection of illumination light from the distal ends of the fibers can impose limitations on the dynamic range; fiber autofluorescence can also have confounding effects.

Single-fiber solutions require an actuation method to move the fiber tip at the distal end of the probe. Methods employing piezomotors, microelectromechanical systems (MEMS), and tuning-forks have been investigated. In most of these approaches, the objective lens system in front of the fiber distal end is not actuated, which results in constraints on the achievable numerical aperture (NA) and the FOV of the scanner.

Recently, a novel, hand-held microscopy probe for acquiring confocal images of biological tissue was presented by B. H. W. Hendriks, et al., in "*High-resolution resonant and nonresonant fiber-scanning confocal microscope*", J. Biomed. Optics 16 (2011), 026007.

This microscopy probe generates images by scanning a fiber-lens combination with a miniature electromagnetic actuator, which allows it to be operated in resonant and nonresonant scanning modes. In the resonant scanning mode, a circular field of view with a diameter of 190 µm and an angular frequency of 127 Hz can be achieved. In the nonresonant scanning mode, a maximum field of view with a width of 69 µm can be achieved. The measured transverse and axial resolutions are 0.60 and 7.4 µm, respectively. Images of biological tissue acquired in the resonant mode demonstrate its potential for real-time tissue differentiation. With an outer diameter of only 3 mm, the microscopy probe could be utilized to visualize cellular microstructures in vivo across a broad range of minimally-invasive procedures.

However, the fact that the objective must be small in size in combination with the high-NA results in a small free working distance (FWD), i.e. the distance from the last lens surface facing the object to the focal point where the object is. This working distance is in general significantly smaller than the diameter of the needle. A resulting drawback of the microscopy probe scanning fiber system is that it can only inspect the tissue in the forward direction and effectively not in other directions because of the small free working distance; hence the field of view is inherently limited.

The inventors of the present invention have appreciated that an improved optical microscopy probe for scanning microscopy imaging of an associated object is of benefit, and has in consequence devised the present invention.

SUMMARY OF THE INVENTION

It would be advantageous to achieve an improvement in the obtainable field of view (FOV) for an optical microscopy probe for scanning microscopy imaging. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention is presented an optical microscopy probe for scanning microscopy imaging of an associated object (O), the probe comprising:

a housing with an optical window, the optical window being positioned at a side position at the distal end of the housing, an optical guide having an objective lens rigidly coupled to an end portion of the optical guide, the optical guide being displaceably mounted in a transverse direction of the housing so as to enable optical scanning in a region of interest (ROI) outside said optical window, and a relay lens unit rigidly mounted relative to the housing at the distal end of the probe, the relay lens unit comprising a first lens, a second lens and a mirror, wherein the relay lens unit is optically arranged relative to the objective lens for allowing scanning microscopy through the optical window of the housing.

The invention is particularly, but not exclusively, advantageous for obtaining an improvement in the obtainable the field of view of the probe because the cooperation between the displaceable objective lens and the relay lens unit may compensate, at least in part, for the relative limited free working distance of the objective lens. The present invention mitigates this drawback and enables imaging in places and/or directions hitherto not accessible by scanning microscopy imaging using an optical microscopy probe. For instance in order to determine vulnerable plaque in a blood vessel the wall of the blood vessel should be imaged which requires e.g. sideward looking microscopic fiber scanning imaging as enabled by the teaching of the present invention. Thus, the invention may enable more flexibility with respect to regions of interest (ROI) that are available for scanning microscopy imaging around the microscopy probe.

It is therefore believed that the present invention may facilitate particular advantageous microscopic imaging possibilities not previously possible, and this may, in turn, provide information to medical personal enabling diagnostic and therapeutic improvements.

It may further be noted that it is in fact surprising that it is actually possible to have a relay lens unit at a distal position of the probe considering that the relay lens unit for optimal performance should have a numerical aperture (NA) that is comparable to the numerical aperture of the objective lens. Thus, a rather compact design is needed for the relay lens unit at the distal position of the probe. In optics, a relay lens may generally be defined as a lens or lens group that inverts an image and extends the optical path.

In the context of the present invention, the concept of a "probe" is to be considered and understood in a broad sense including, but not limited to, an instrument or device for exploration into matter or environments of limited accessibility, or a slender instrument or device for medical examination of patients. Thus, the probe may have a transverse dimension D, e.g. diameter, of maximum 1, 2, 3, 4, or 5 millimeter depending on the application.

In the context of the present invention it is also to be understood that the term "optical guide" may include, and is not limited to, optical fibers (multi-mode and single-mode), thin film optical paths, photonic crystal fibers, photonic bandgab fibers (PBG), polarization maintaining fibers, etc. The probe may also comprise more than one optical guide e.g. a plurality of fibers or a fiber bundle.

In the context of the present invention, it further to be understood that the concept of microscopic imaging involves the application of lenses to magnify parts of the observed associated object. In some embodiment, the optical microscopy probe is adapted for confocal microscopy but other optical microscopy modes are also contemplated. In particular, the present invention may provide magnification of at least 40 times, preferably at least 60 times, more preferably at least 80 times.

Advantageously, the housing of the optical microscopy probe may have an elongated shape, the optical window being arranged for optical microscopy in a direction substantially perpendicular to a longitudinal direction of the probe, i.e. the optical microscopy imaging will be performed in a sidewards direction relative to the longitudinal direction of the probe, at least as seen from the distal portion or end of the probe. It is to be understood that the central optical path of this sidewards direction looking embodiment may also deviate from the said perpendicular direction with about 5, 10, 20, 30 degrees (in both directions) depending on the desired imaging direction.

In another advantageous embodiment, the housing of the optical microscopy probe may have an elongated shape with a tapering distal end, the optical window being positioned at said tapering distal end of the probe. Thus, the probe may have a needle-like shape with the optical window positioned at the tapering or apex portion of the probe. In this configuration the optical window will typically be suitable for viewing in a direction in between a frontal direction and a perpendicular direction, relative to the elongated shape of the probe, the direction typically depending on the angle of the apex section of the probe.

Preferably, the optical guide may be transversally displaceable by one or more actuators positioned in the probe for enabling scanning microscopy imaging.

Typically, the optical lens may have a free working distance which is significantly smaller than a transverse dimension of the probe, which makes the use of the present invention more desirable. The free working distance may be below 0.1%, 1%, or 10% of the transverse dimension of the probe, e.g. maximum diameter or average diameter of the probe.

Beneficially, the numerical aperture (NA) of the objective lens may be at least approximately 0.4, preferably at least approximately 0.6, more preferably at least approximately 0.8 for sufficient optical resolution and imaging.

Typically, the first lens of the relay lent unit may be positioned with an optical axis substantially parallel with a longitudinal direction of the probe to facilitate a compact optical design of the probe. Additionally, the first lens of the relay lens unit may have an optical entrance diameter of at least 50% of a transverse dimension of the probe, e.g. maximum diameter or average diameter of the probe. One normally desires a large first lens in the relay lens unit to optically match the objective lens.

In most configurations, the second lens may define a focal point of microscopic imaging outside of the probe.

In some embodiments, it is contemplated that the functionality of the relay lens unit may be performed in one single lens, i.e. a combination of the first and the second lens.

In one design of the relay lens unit, the second lens may be optically arranged relative to the mirror so that an optical path for microscopic imaging, going through and out of the relay lens unit, is first entering and exiting the second lens, and subsequently reflected by the mirror i.e. that the light arrives to second lens first, and then to mirror.

In another design of the relay lens unit, the second lens may be optically arranged relative to the mirror so that an optical path for microscopic imaging, going through and out of the relay lens unit, is first reflected by the mirror, and subsequently enters and exits the second lens i.e. that the light arrives to the mirror first, and then to the second lens.

In yet another design of the relay lens unit, wherein the second lens may be optically arranged relative to the mirror so that an optical path for microscopic imaging, going through and out of the relay lens unit, is first entering the second lens, and then subsequently reflected by the mirror, the mirror being optically integrated into the second lens, and then exits the second lens, i.e. that the light arrives to the second lens first, and then within the second lens is reflected by the integrated mirror and the finally exits the second lens. The second lens preferably may have a fold mirror positioned within the lens.

For some applications, the optical probe may form part of an endoscope, a catheter, a needle, a biopsy needle, or other similar application as the skilled person will readily realized, e.g. in connection with cancer diagnosis, monitoring wound healing or studying molecular processes in tissue.

A second aspect of the present invention relates to a system for performing for scanning microscopy imaging of an associated object (O), the system comprising:

an optical microscopy probe, wherein the probe comprises a housing with an optical window, the optical window being positioned at a side position at the distal end of the housing, an optical guide having an objective lens rigidly coupled to an end portion of the optical guide, the optical guide being displaceably mounted in a transverse direction of the housing so as to enable optical scanning in a region of interest (ROI) outside said optical window, and a relay lens unit rigidly mounted relative to the housing at the distal end of the probe, the relay lens unit comprising a first lens, a second lens and a mirror, wherein the relay lens unit is optically arranged relative to the objective lens for allowing scanning microscopy through the optical window of the housing, an irradiation source arranged for optical communication with said optical microscopy probe and arranged for scanning microscopy imaging, and an image detector arranged for optical communication with said optical microscopy probe and arranged for scanning microscopy imaging detection.

In a third aspect, the present invention relates to a method for performing scanning microscopy imaging of an associated object (O) with an optical microscopy probe, the method comprising:

providing an optical microscopy probe with an optical window in a housing, the optical window being positioned at a side position at the distal end of the housing, providing an optical guide having an objective lens rigidly coupled to an end portion of the optical guide, the optical guide being displaceably mounted in a transverse direction of the housing so as to enable optical scanning in a region of interest (ROI) outside said optical window, and providing a relay lens unit rigidly mounted relative to the housing at the distal end of the probe, the relay lens unit comprising a first lens, a second lens and a mirror, wherein the relay lens unit is optically arranged relative to the objective lens for allowing scanning microscopy through the optical window of the housing.

It is also contemplated that fields of application may include, but is not limited to, fields where miniature imaging devices are useful, such as in connection with inspection of small-scale devices, etc.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
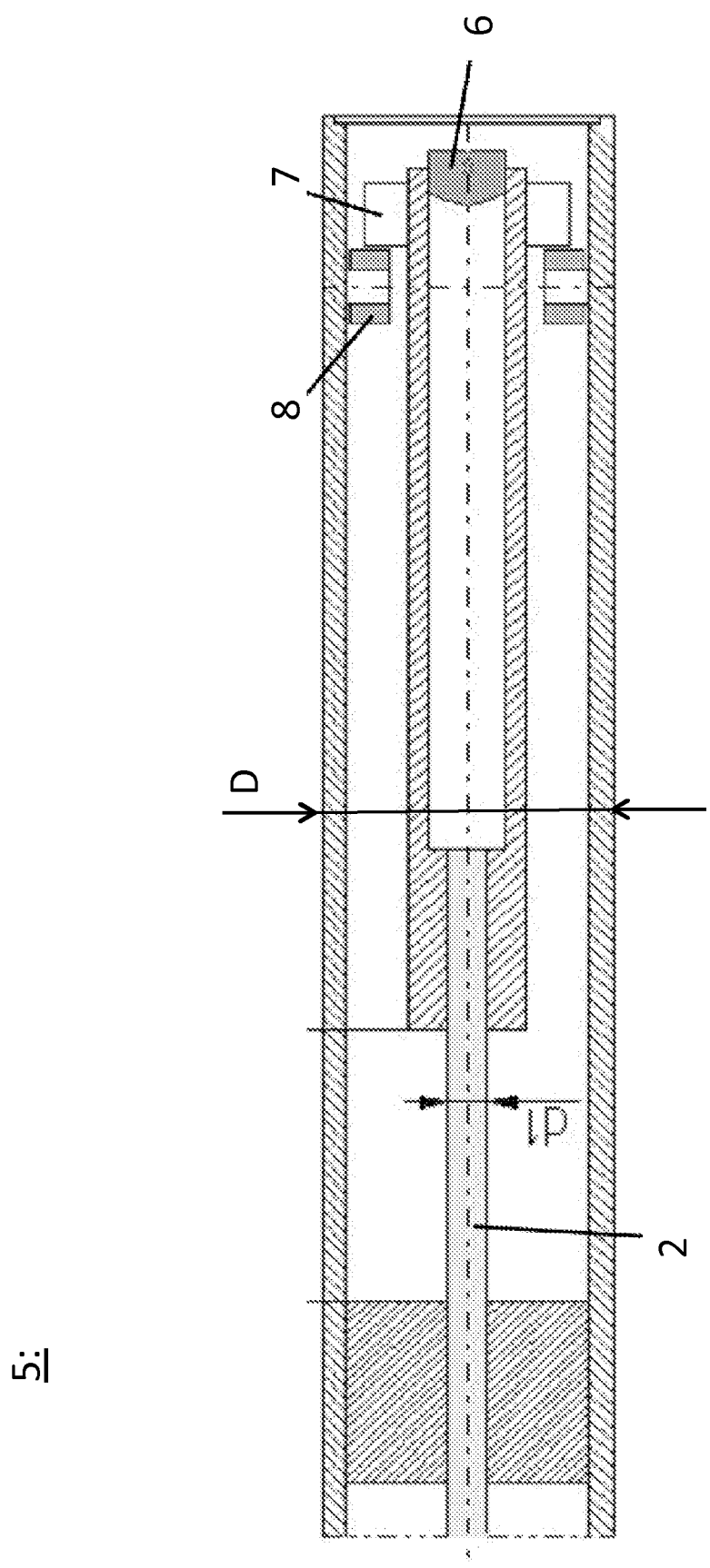
FIG. 1 is a scanning microscopy probe known in the art.

FIG. 1 is a scanning microscopy probe 5 known in the art as explained in B. H. W. Hendriks (also one of the present inventors), et al., in "*High-resolution resonant and nonresonant fiber-scanning confocal microscope*", J. Biomed. Optics 16 (2011), 026007, which is hereby incorporated by reference in its entirety. The skilled reader is referred to this reference for implementing a scanning microscopy probe where the optical guide 2, e.g. optical fiber, has at its distal end an objective lens 6 rigidly mounted. The lens 6 is displaced by actuators 8, e.g. electromagnetic coil, cooperating with magnets mounted on the side of the optical guide 2. The probe 5 allows microscopic tissue inspection at the tip of the needle and can be applied in various medical applications. In order to achieve this microscopic inspection the objective lens 6 used in the scanner probe 5 must have a high numerical aperture (NA). The fact that the objective must be small in size in combination with the high-NA results in a small free working distance.

A drawback of the current scanning fiber probe 5 is that is can only inspect the tissue in the forward direction and effectively not in the sideward direction because of the small free working distance. This working distance is in general smaller than the diameter D of the needle or probe 5. When using the device 5 in for instance a blood vessel the capability to monitor other directions is important. For instance in order to determine vulnerable plaque in a blood vessel the wall of the blood vessel should be imaged which requires sideward looking microscopic imaging.

For explaining the present invention the teaching and principle of the above reference will be assumed to known and understood, and like references will be applied below.

Figure 2:
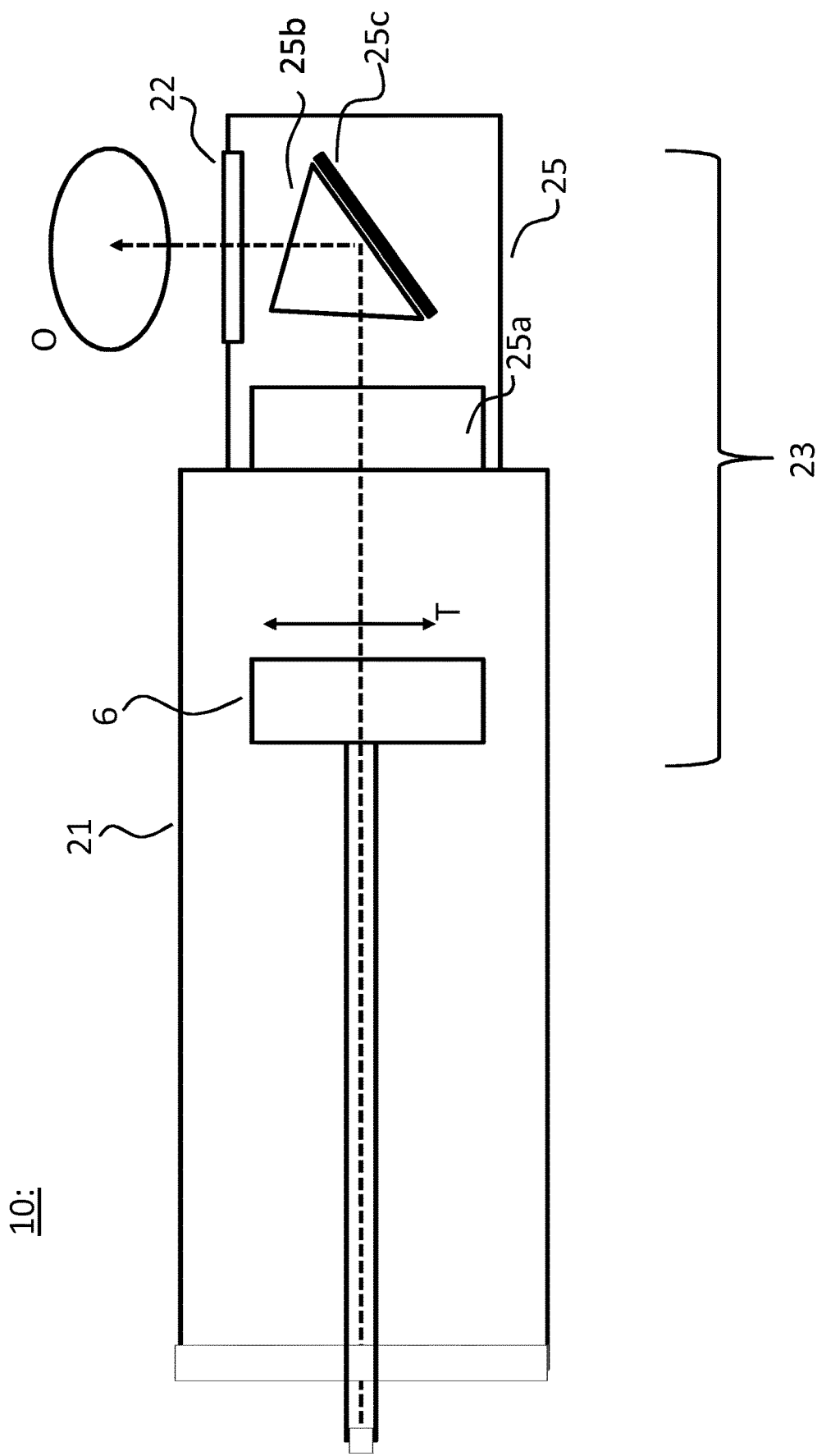
FIG. 2 shows a schematic cross-sectional drawing of an embodiment of the microscopy probe according to the present invention.

FIG. 2 shows a schematic, cross-sectional drawing of an embodiment of the microscopy probe 10 according to the present invention. The optical microscopy probe for scanning microscopy imaging is capable of imaging an associated object O near its distal end. For clarity only an end section of the probe 10 is shown and only selected elements and features for explaining the teaching and principle of the present invention.

The probe 10 comprises a housing 21 with an optical window 22, the optical window being positioned at a side position at the distal end 23 of the housing.

An optical guide 2 has an objective lens rigidly coupled to an end portion of the optical guide, the optical guide being displaceably mounted in a transverse direction of the housing, as indicated by double-headed arrow T, so as to enable optical scanning in a region of interest (ROI) outside said optical window 22. The region of interest is thus defined by the transverse scanning and the optics of the probe 10.

A relay lens unit 25 is rigidly mounted relative to the housing 21 at the distal end 23 of the probe 10 and it thus fixed during scanning with the lens 6. The relay lens unit 25 comprises a first lens 25a, a second lens 25b and a mirror 25c, wherein the relay lens unit 25 is optically arranged relative to the objective lens 6 for allowing scanning microscopy through the optical window 22 of the housing 21. Thus, as shown by the dotted outward going optical path through the lens 6 and the first lens 25a, the second 25b lens and reflected by the mirror 25c, the object O can be imaged by the microscopy probe 10.

The housing 21 and relay lens unit 25 can be separate entities or they can be part of the same entity. As schematically illustrated in FIG. 2, the outer diameter of the housing 21 can be larger than the outer diameter of the relay lens unit 25, but it can also be vice versa, or the outer diameter can be substantially the same. For minimal medical invasive inspection, it is of course important that both diameters are small.

Figure 3:
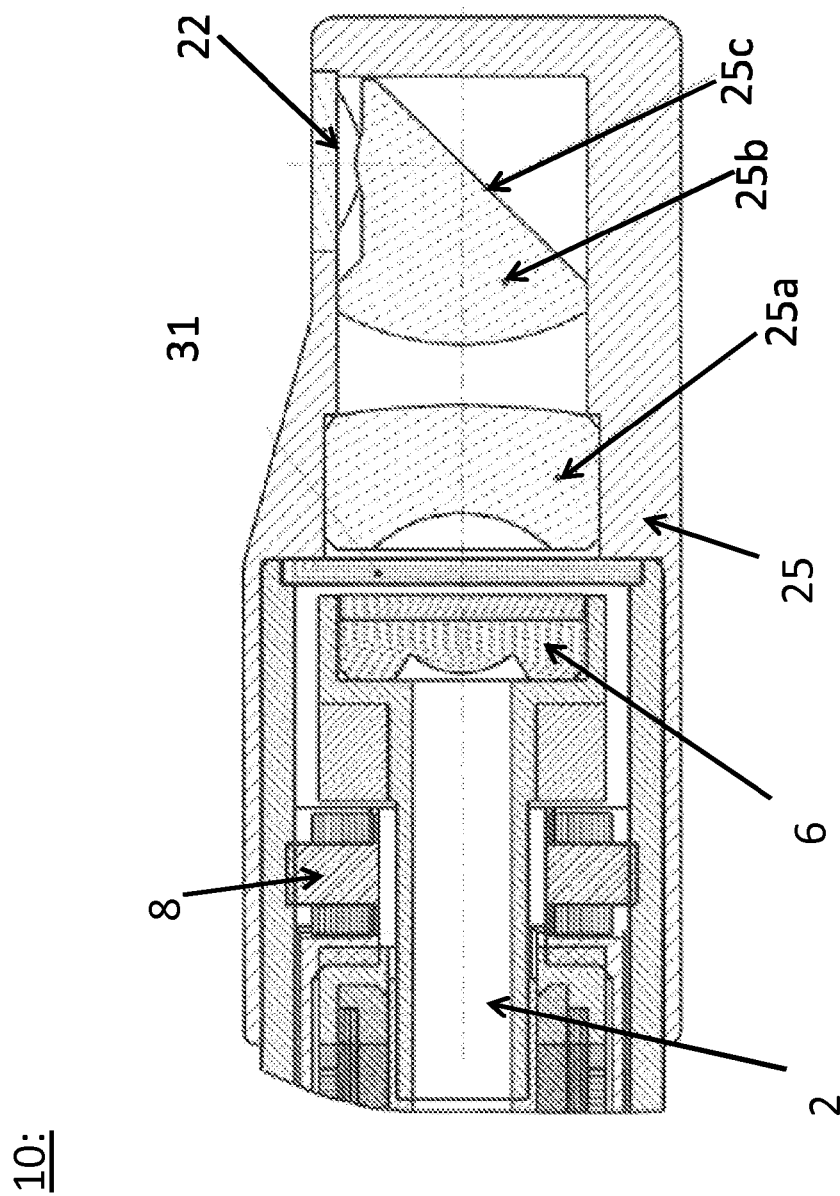
FIG. 3 shows a more detailed, cross-sectional illustration of an embodiment of a microscopy probe according to the present invention.

FIG. 3 shows a more detailed, cross-sectional illustration of an embodiment of a microscopy probe 10 according to the present invention. The relay lens units comprises of two lenses 25a and 25b. The first lens 25a has a diameter of almost the outer diameter of the fiber scanner 10. It translates the focal plane of the fiber original scanner into a substantially parallel beam. This parallel beam is then focused by a second lens 25b to the sideward direction. In order to do this a fold mirror 25c is integrated in the second lens in order to deal with the small free working distance issue. As can be observed in FIG. 3, it is indeed now possible to relay the focal point of the original fiber scanner to a sideward position beyond the sidewall of the fiber scanner 10.

Making use of lenses in the relay lens system 25 with similar size of the outer dimension of the fiber scanner is beneficial because of two reasons: (1) the larger size allows to have a substantial field of view (FOV) that is required in order to cover the relay of the imaging field fiber scanner, (2) it allows relaying the image to the sideward direction i.e. there is space enough to focus the image outside the scanner at the sideward direction. The relay lens elements 25a, 25b, and 25c, are fixed in a mount that has the outer dimension of the fiber scanner probe 10. For optimum performance the NA of the relay lens unit 25 is adjusted to the NA of the objective lens 6 i.e. NA of relay unit 25 is similar in size to the NA objective lens 6. In front of the second element containing the fold mirror a thin glass window 31 is present such that the relay elements are fully enclosed in the mount. This prevents damaging of the said elements and allows easy cleaning of the system.

FIGS. 4A-4D show four views of optical modeling performed of the microscopy probe 10 according to the present invention. The modeling corresponds to the embodiment shown in FIG. 3 and consists of so-called ray trace plots of the optical design of the relay lens unit 25 with an integrated fold mirror 25c into the second lens 25b as shown in FIG. 3.

Figure 4A:
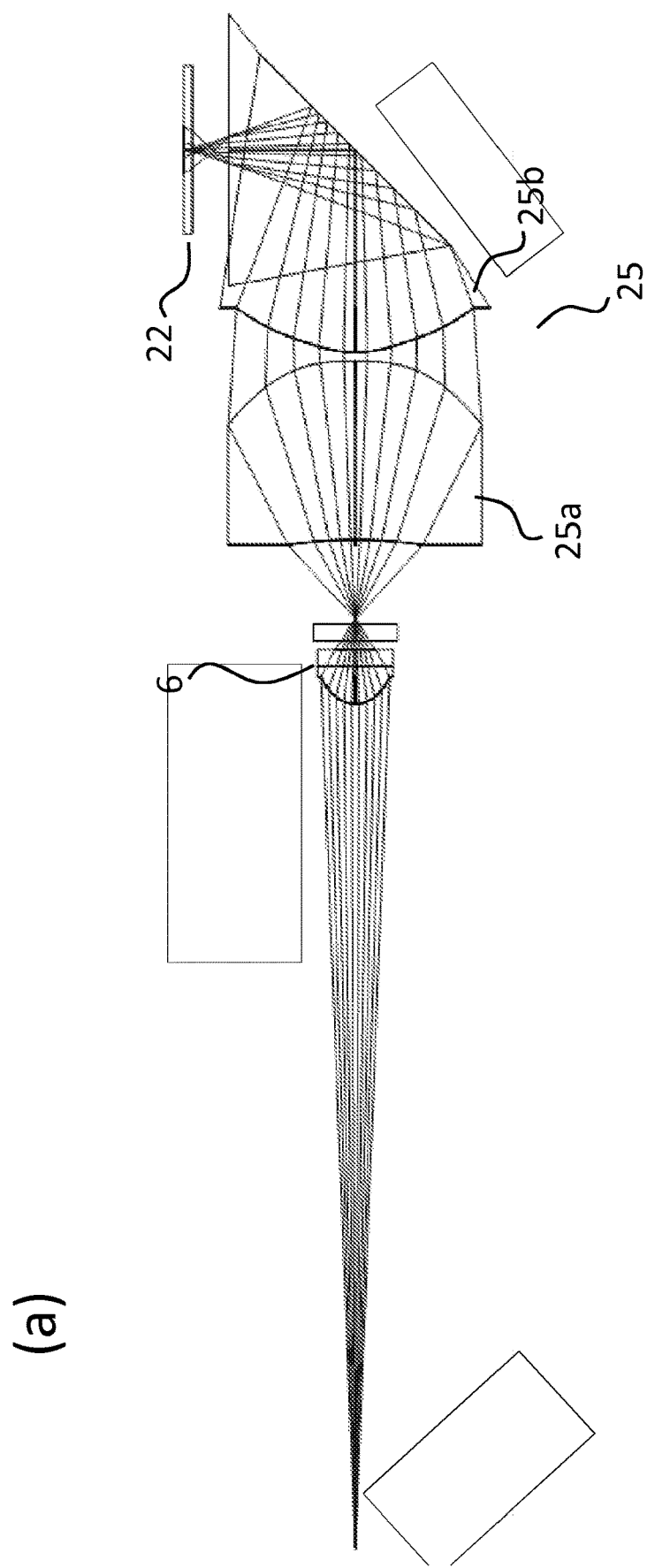
FIGS. 4A-4D show four views of optical modeling performed of the microscopy probe according to the present invention.

In FIG. 4A there is shown a planar overview of the beam having left the fiber (not shown) is being focuses by the objective 6 to a focal point just in front of the scanner. The relay lens unit 25 then refocuses this image sideward by employing lenses 25a and 25b with integrated an fold mirror 25c.

Figure 4B:
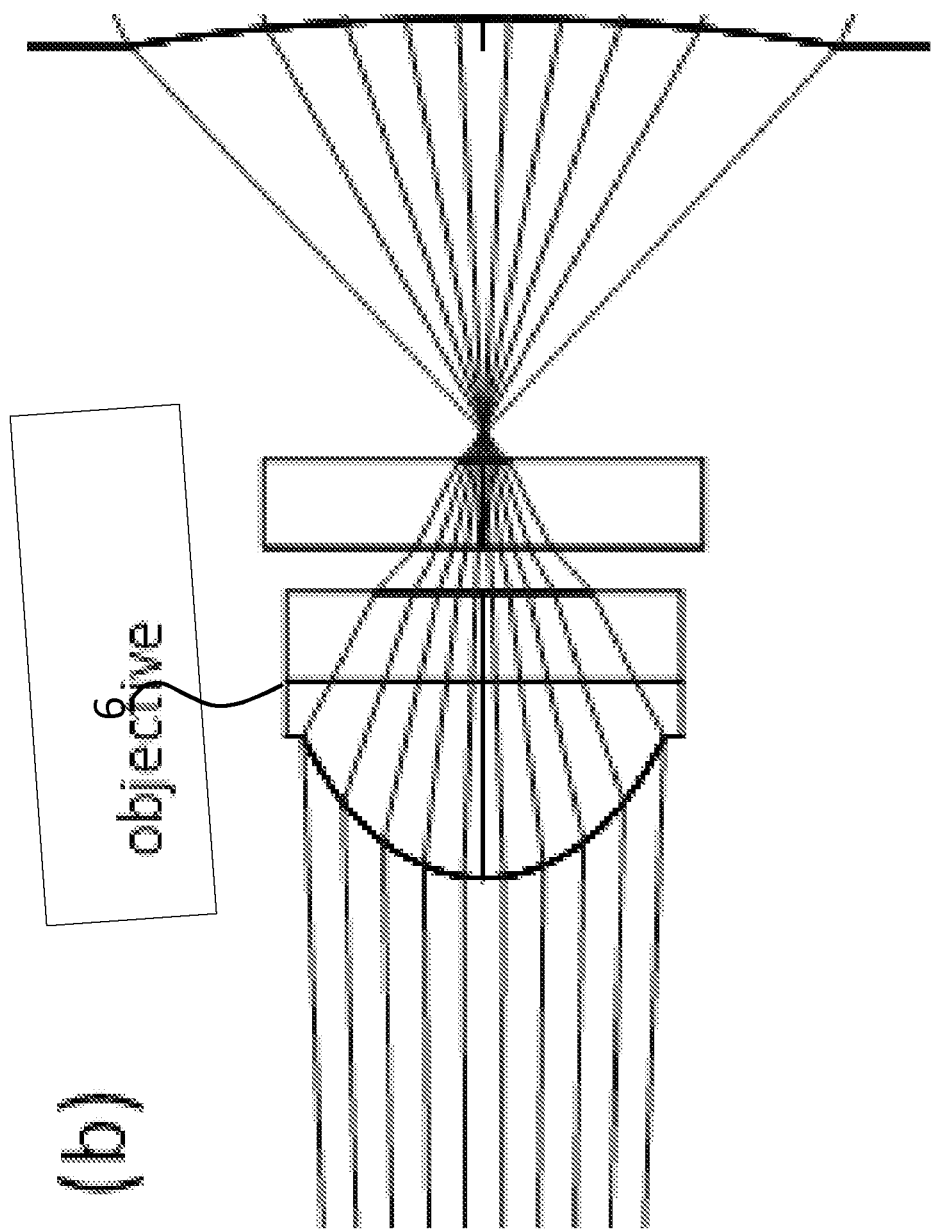
Figure 4C:
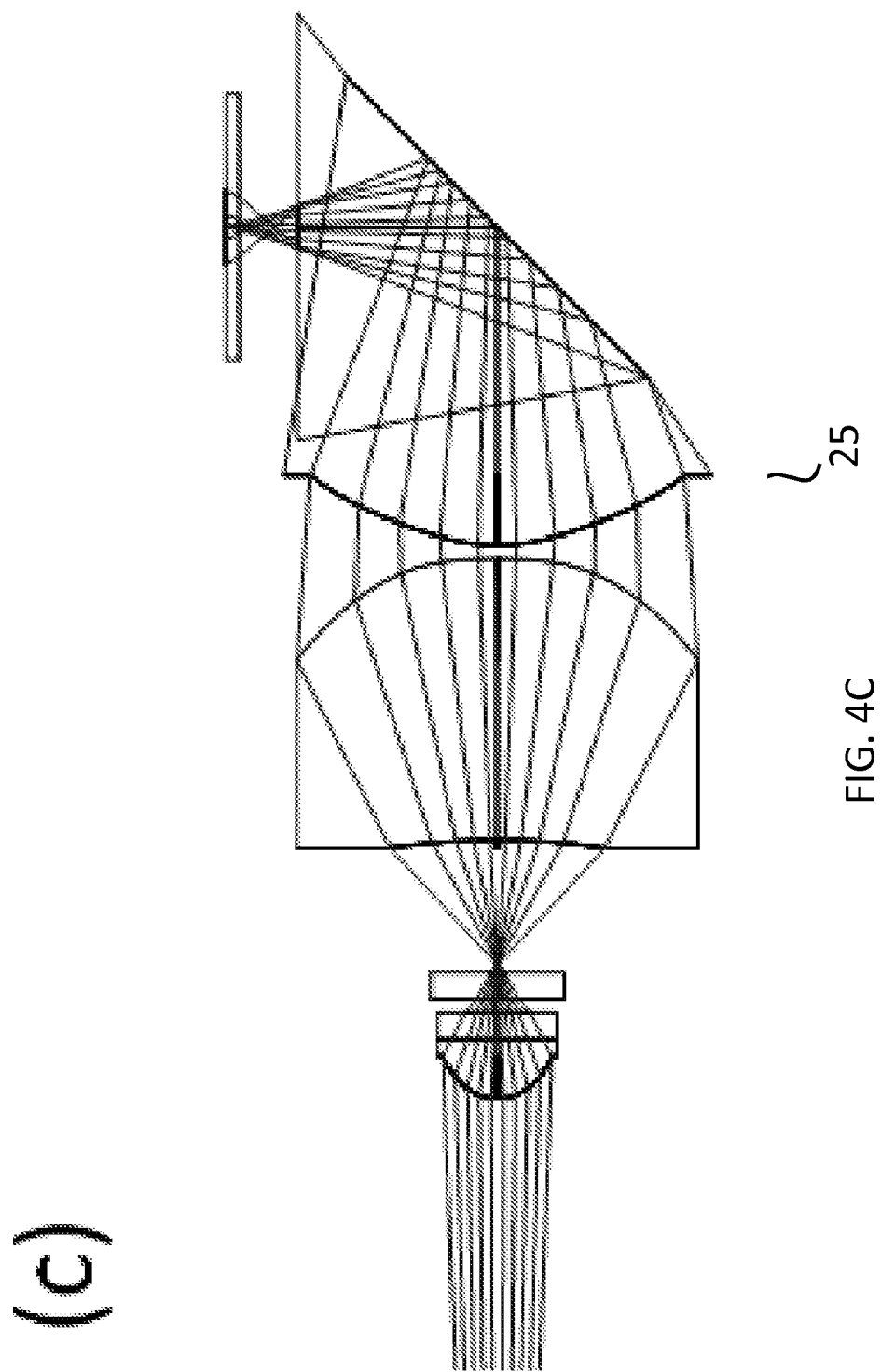

In FIG. 4B and FIG. 4C closer views are provided of the objective lens 6 and the relay lens unit 25 and the optical modeling performed of their respective the ray trace plots.

Figure 4D:
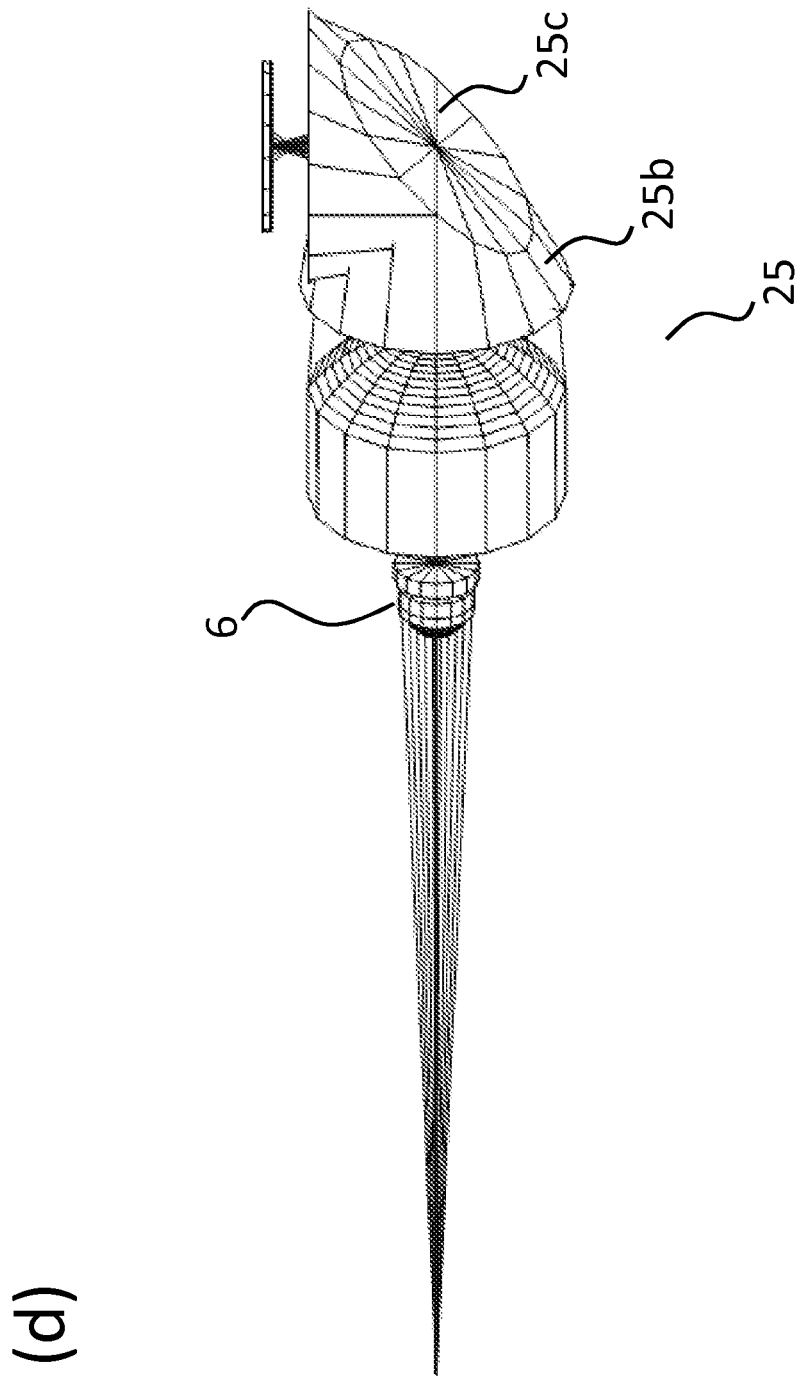

FIG. 4D is a perspective view of the optical modeling of the lens 6 and the relay lens unit 25. In this view, the integrated fold mirror 25c is also shown forming part of the second lens 25b.

Figure 5:
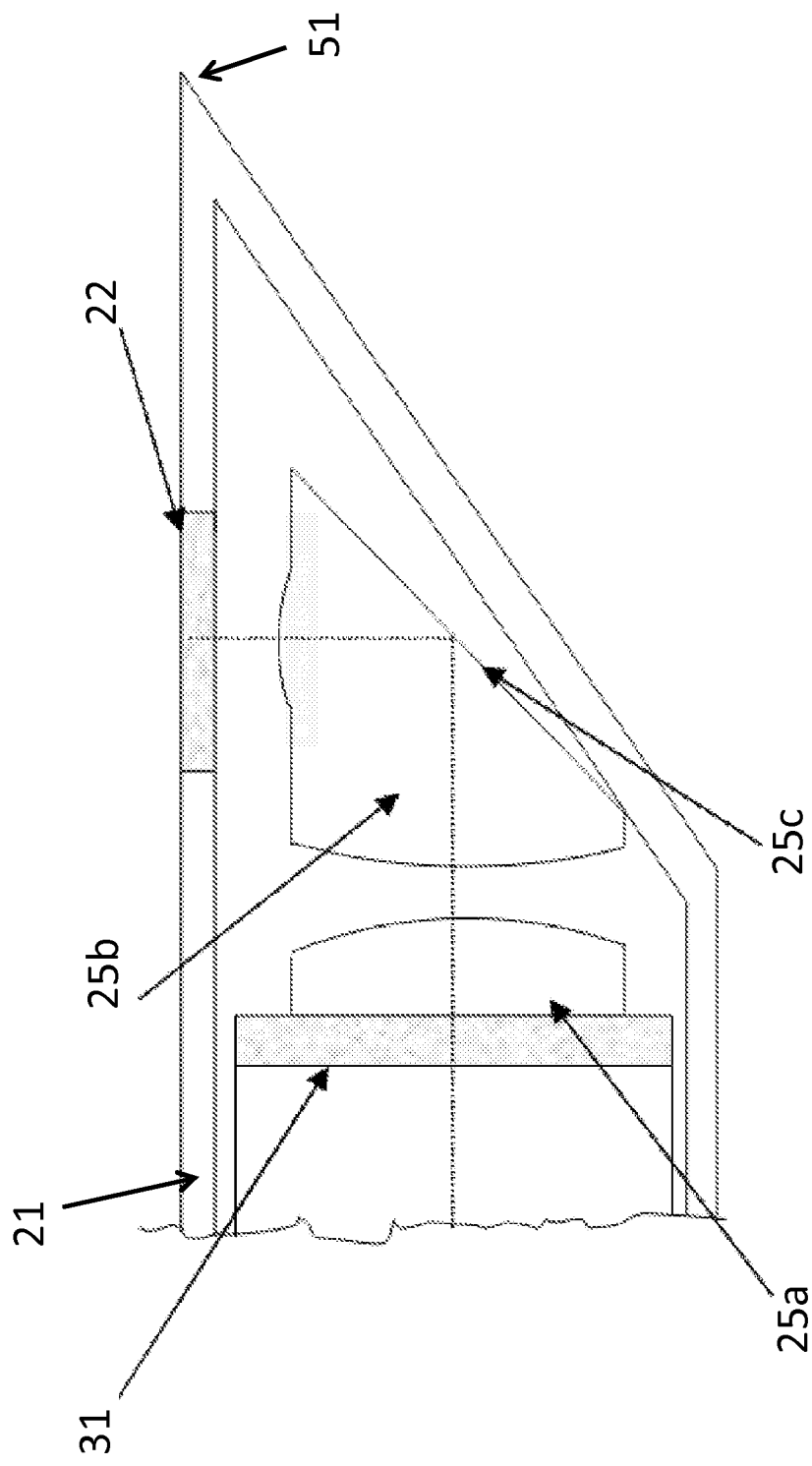
FIGS. 5, 6 and 7 are schematic cross-sectional drawings of other embodiments of the microscopy probe according to the present invention.
Figure 6:
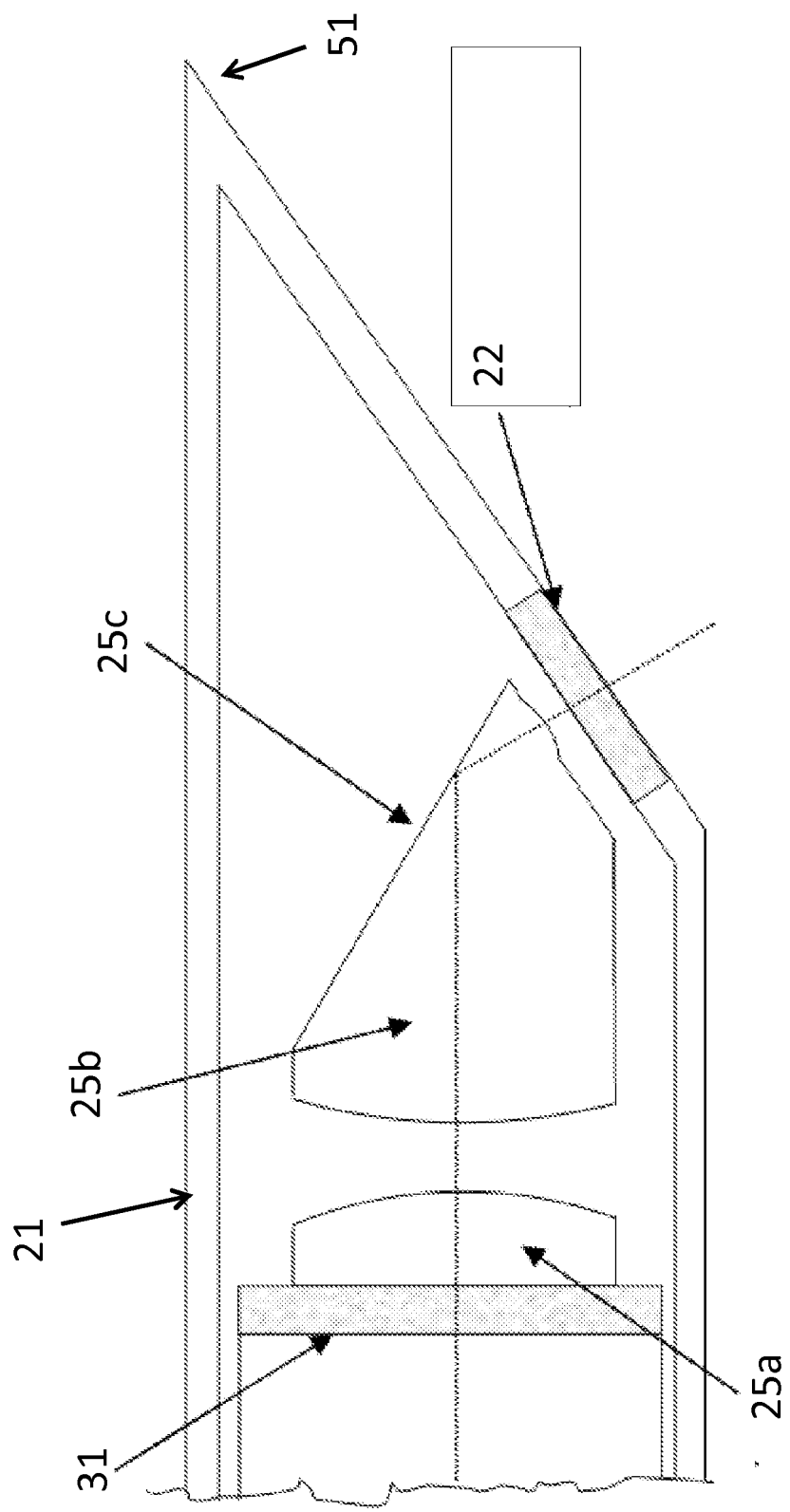
Figure 7:
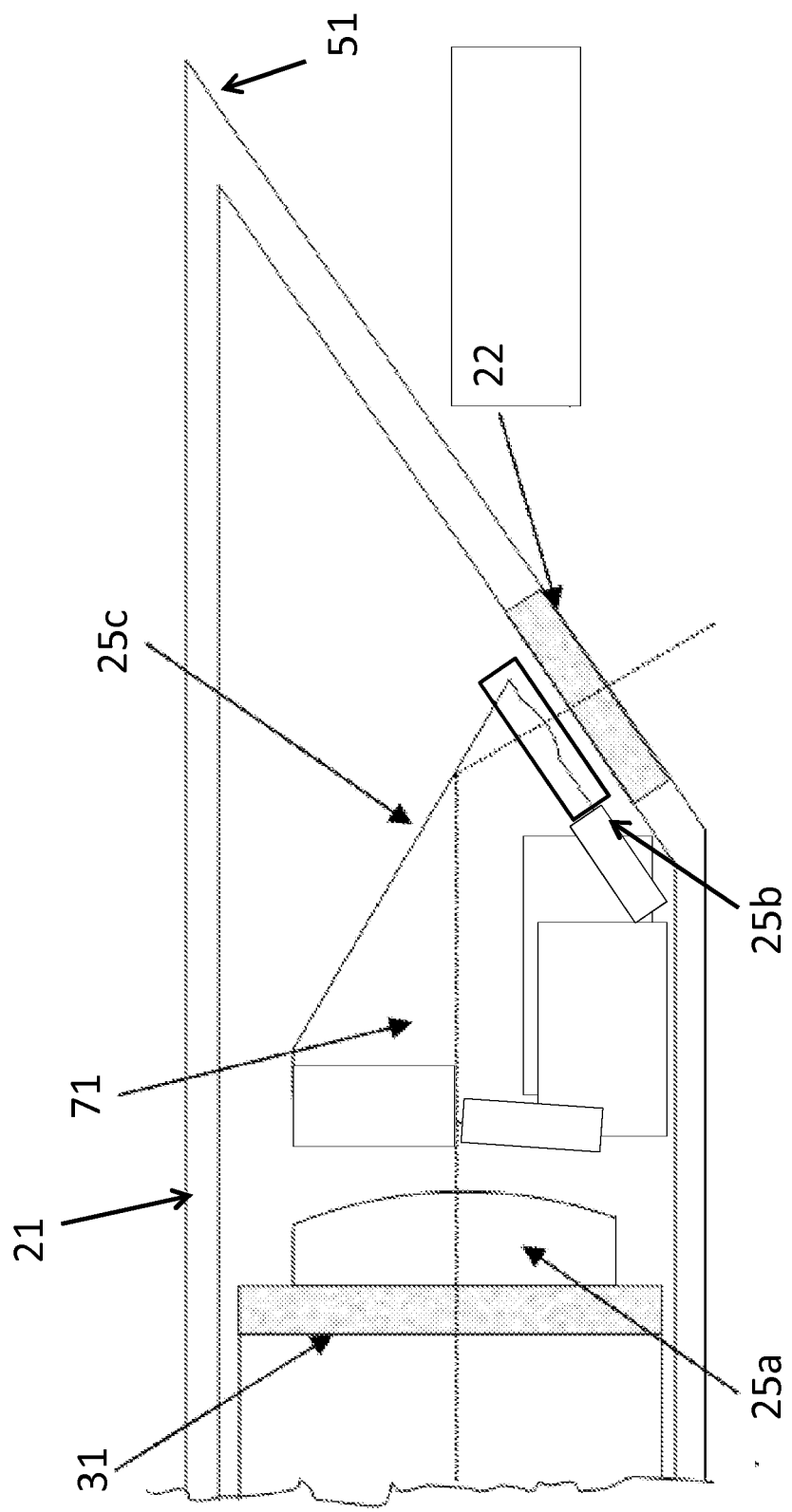

FIGS. 5, 6 and 7 are schematic cross-sectional drawings of other embodiments of the microscopy probe 10 according to the present invention.

In FIG. 5, an embodiment is shown, wherein the housing 21 of the optical microscopy probe 10 has an elongated shape and the optical window 22 is arranged for optical microscopy in a direction substantially perpendicular to a longitudinal direction of the probe i.e. this enables sideward microscopic imaging. On opposite side of the window 22, the probe has an inwardly tapering profile ending in a point-like end 51 like a needle suitable for medical inspection.

In FIG. 6, another embodiment is shown 2 where the window 22 is positioned on an inwardly tapering profile. The profile enables a needle-like design where the tapering profile ends at 51. This embodiment enables microscopic imaging in a direction between a strictly sideward direction (as with the embodiment of FIG. 5) and forward direction.

FIG. 7 is similar to the embodiment of FIG. 6, but in this embodiment the relay lens unit 25 is designed to facilitate that the second lens 25b is optically arranged relative to the mirror 25c so that an optical path 71 for microscopic imaging, going through and out of the relay lens unit 25, is first reflected by the mirror, and subsequently enters and exits the second lens.

Figure 8B:
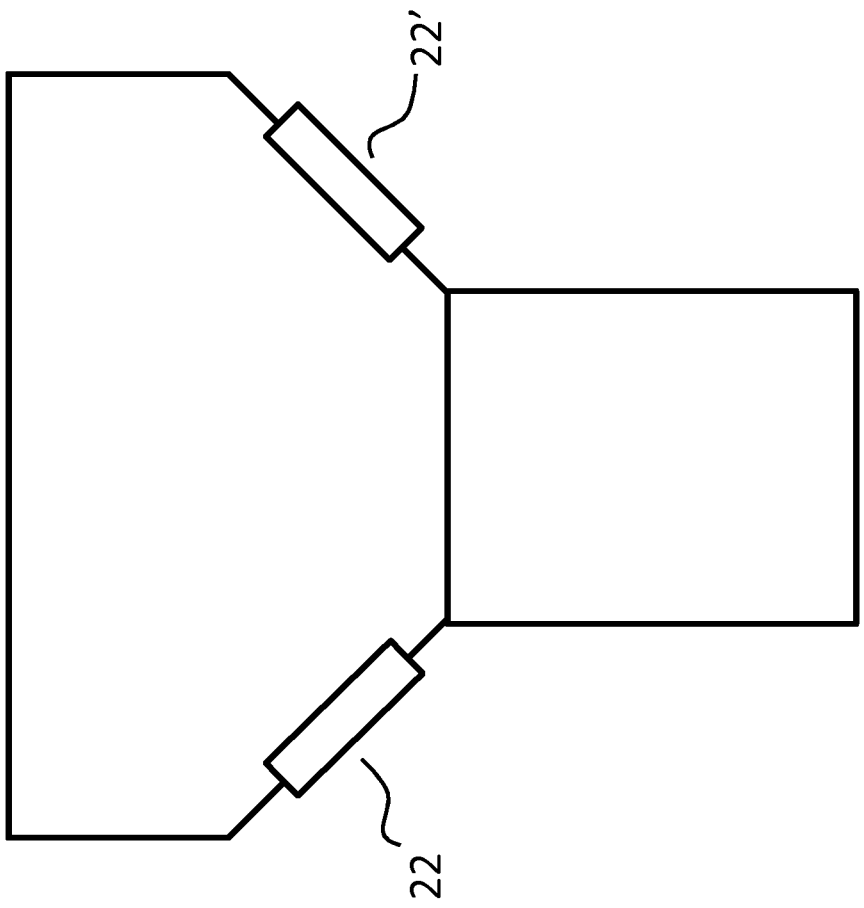
FIGS. 8A-8B are schematic cross-sectional drawings of two different distal end geometries of the microscopy probe according to the present invention.
Figure 8A:
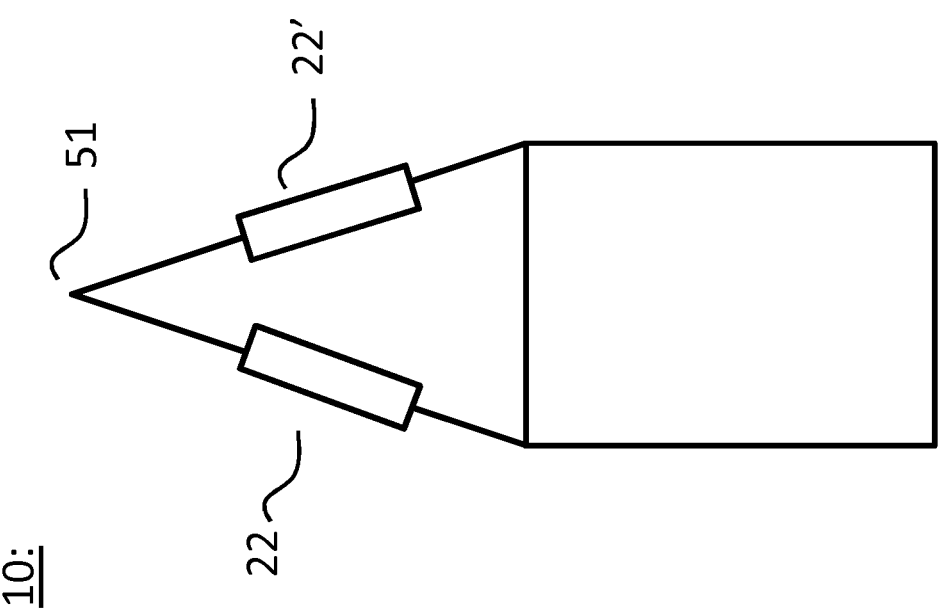

FIGS. 8A-8B are schematic cross-sectional drawings of two different distal end geometries of the microscopy probe according to the present invention. In FIG. 8A, the probe is tapered inwardly towards a point-like end 51. In FIG. 8B, the probe is tapered outwardly where the windows 22 and 22' are positioned. This enables some degree of backward looking depending on outwardly tapering angle relative to a longitudinal direction of the probe. In these embodiments, two windows 22 and 22' are shown but even more windows may be contemplated within the teaching and principle of the present inventions, Nevertheless, for minimal invasive inspection, an overall constraint is of course the overall outer dimension of the probe 10, which also limits the number of windows possible to a certain degree.

Figure 9:
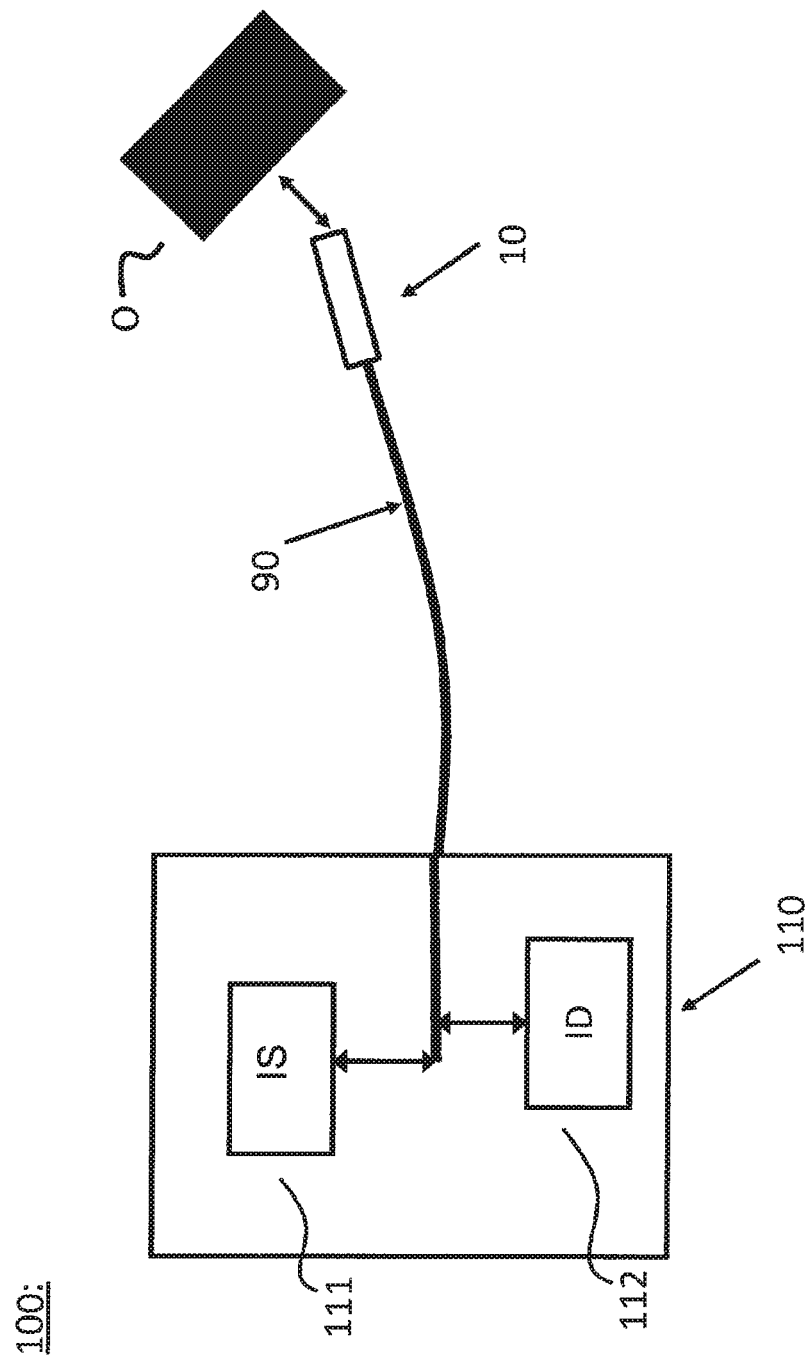
FIG. 9 shows a schematic drawing of an embodiment of a system for performing optical microscopy with a microscopy probe according to the present invention.

FIG. 9 shows a schematic drawing of an embodiment of a system 100 for performing optical microscopy with a microscopy probe 10 according to the present invention. The probe 10 is operatively and optically communicating with imaging module 110 as shown by optical connection 90, e.g. an encapsulated optical guide, such as a catheter or similar devices. The optical microscopy probe 10 is shown in front of the object O to be examined. Also shown is an irradiation source 111 IS arranged for outputting an appropriate electromagnetic type or irradiation for microscopic imaging, e.g. visible laser light, and for optical communication, as schematically indicated by the double-headed arrow, with said optical microscopy probe 10, and thus arranged for scanning microscopy imaging. Additionally, an image detector 112 ID is arranged for optical detection of resulting reflected light from the object O, e.g. a CCD image sensor, and for optical communication, as schematically indicated by the other double-headed arrow, with said optical microscopy probe 10 and arranged for scanning microscopy imaging detection. For further details, the skilled reader is referred to B. H. W. Hendriks (also one of the present inventors), et al., in "*High-resolution resonant and nonresonant fiber-scanning confocal microscope*", J. Biomed. Optics 16 (2011), 026007, which is hereby incorporated by reference in its entirety.

Figure 10:
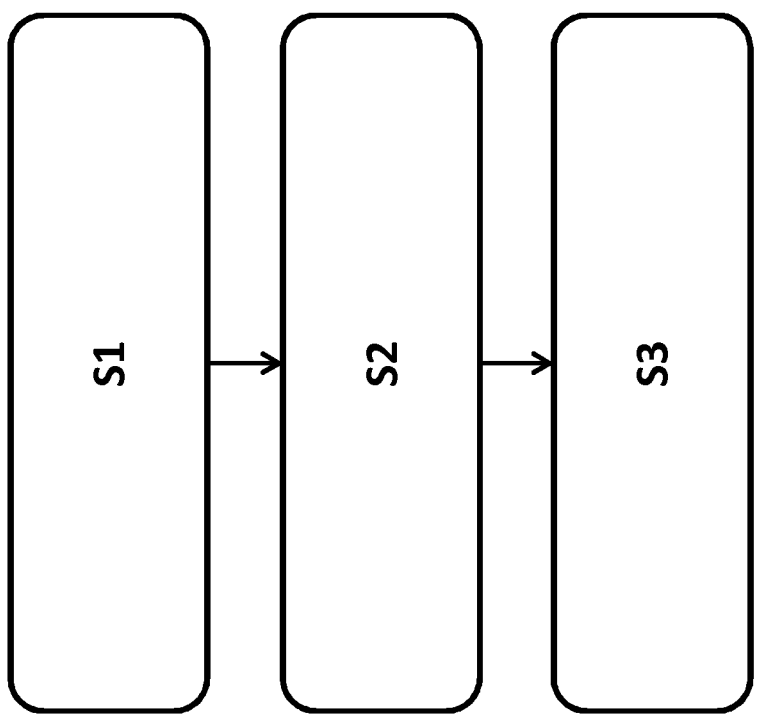
FIG. 10 is a flow chart of a method according to the invention.

FIG. 10 is a flow chart of a method according to the invention. The method for performing scanning microscopy imaging of an associated object O with an optical microscopy probe 10 comprises the steps of:

S1 providing an optical microscopy probe with an optical window in a housing, the optical window being positioned at a side position at the distal end of the housing, S2 providing an optical guide having an objective lens rigidly coupled to an end portion of the optical guide, the optical guide being displaceably mounted in a transverse direction of the housing so as to enable optical scanning in a region of interest ROI outside said optical window, and S3 providing a relay lens unit rigidly mounted relative to the housing at the distal end of the probe, the relay lens unit comprising a first lens, a second lens and a mirror, wherein the relay lens unit is optically arranged relative to the objective lens for allowing scanning microscopy through the optical window of the housing.

In short, the present invention discloses an optical microscopy probe 10 for scanning microscopy imaging of object O.

The probe has an optical window 22, and an optical guide 2 having an objective lens 6 rigidly coupled to an end portion of the optical guide. The optical guide is displaceably mounted in a transverse direction of the housing 21 so as to enable optical scanning in a region of interest (ROI). A relay lens unit 25 is rigidly mounted at the distal end 23 of the probe and it has a first lens 25a, a second lens 25b and a mirror 25c, the relay lens unit being optically arranged relative to the objective lens for allowing scanning microscopy through the optical window of the housing. The invention is advantageous for obtaining an improvement in the available field of view of the probe because the cooperation between the displaceable objective lens and the relay lens unit may compensate, at least in part, for the relative limited free working distance of the objective lens.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An optical microscopy probe for optical scanning of an associated object, the probe comprising:
    an elongated housing with an optical window, wherein the optical window is positioned at a side position at a distal end of the housing for providing an optical path outside the probe having a direction different from a longitudinal direction of a longitudinal axis of the probe, the distal end being closer to the associated object than a proximal end of the housing;
    an optical guide having an objective lens rigidly coupled to an end portion of the optical guide;
    an actuator configured to move the optical guide together with the objective lens in a transverse direction within the housing to enable the optical scanning in a region of interest outside said optical window; and
    a relay lens rigidly mounted to the housing, wherein the relay lens is at the distal end of the probe, the relay lens being optically arranged relative to the objective lens for allowing scanning microscopy through the optical window by translating a focal plane of the objective lens into a beam to define a focal point of microscopic imaging outside of the optical window based on the movement of the optical guide by the actuator.

2. The probe according to claim 1, wherein the objective lens has a free working distance which is significantly smaller than a transverse dimension of the probe.

3. The probe according to claim 1, wherein a numerical aperture of the objective lens is at least 0.4.

4. The probe according to claim 1, wherein the relay lens comprises a mirror and a further lens positioned between the objective lens and the mirror and having an optical axis parallel with the longitudinal direction.

5. The probe according to claim 1, wherein the relay lens comprises a mirror and a further lens between the objective lens and the mirror and having an optical entrance diameter of at least 50% of a transverse dimension of the probe.

6. The probe according to claim 1, wherein the relay lens comprises a focusing lens and a mirror, and wherein the focusing lens defines a focal point of the imaging outside of the probe.

7. The probe according to claim 1, wherein the probe forms part of at least one of an endoscope, a catheter, a needle, and a biopsy needle.

8. The probe of claim 1, wherein a numerical aperture of the objective lens is one of at least 0.6 and 0.8.

9. The probe of claim 1, wherein the distal end of the housing includes tapered surfaces that are tapered outwardly, and wherein the distal end includes both the optical window and a further optical window along the tapered surfaces.

10. The probe of claim 1, wherein the relay lens comprises a focusing lens and a mirror, and wherein the mirror is formed on a partial surface of the focusing lens most distal from the objective lens.

11. The probe of claim 1, relay lens comprises a focusing lens and a mirror, and wherein an optical light path from the objective lens to the optical window passes through a first portion of the focusing lens towards the mirror and passes through the optical window from the mirror and a second portion of the focusing lens.

12. A system for performing optical scanning of an associated object, the system comprising:
    an optical microscopy probe, wherein the probe comprises:
        an elongated housing with an optical window, wherein the optical window is positioned at a side position at a distal end of the housing for providing an optical path outside the probe having a direction different from a longitudinal direction of a longitudinal axis of the probe, the distal end being closer to the associated object than a proximal end of the housing,
        an optical guide having an objective lens rigidly coupled to an end portion of the optical guide,
        an actuator configured to move the optical guide together with the objective lens in a transverse direction within the housing to enable the optical scanning in a region of interest outside said optical window, and
        a relay lens rigidly mounted to the housing, wherein the relay lens is at the distal end of the probe, the relay lens being optically arranged relative to the objective lens for allowing scanning microscopy through the optical window by translating a focal plane of the objective lens into a beam to define a focal point of microscopic imaging outside of the based on the movement of the optical guide by the actuator;
    a light source configured to optically communicate with said optical microscopy probe and configured to provide the optical scanning; and
    an image detector configured to optically communicate with said optical microscopy probe and configured to provide scanning microscopy imaging detection.

13. The system of claim 12, wherein the distal end of the housing includes tapered surfaces that are tapered outwardly, and wherein the distal end includes both the optical window and a further optical window along the tapered surfaces.

14. The system of claim 12, wherein the relay lens comprises a focusing lens and a mirror, and wherein the mirror is formed on a partial surface of the focusing lens most distal from the objective lens.

15. The system of claim 12, wherein the relay lens comprises a focusing lens and a mirror, and wherein light from the light source passes from the objective lens to the optical window by passing through a first portion of the focusing lens towards the mirror for reflection by the mirror and passing through a second portion of the focusing lens for exit from the optical window.

16. A method for performing optical scanning of an associated object with an optical microscopy probe, the method comprising:
providing the optical microscopy probe with an optical window in an elongated housing, wherein the optical window is positioned at a distal end of the housing, the distal end being closer to the associated object than a proximal end of the housing;
providing an optical guide having an objective lens rigidly coupled to an end portion of the optical guide;
providing an actuator configured to move the optical guide together with the objective lens in a transverse direction within the housing to enable the optical scanning in a region of interest outside said optical window; and
providing a relay lens rigidly mounted to the housing, wherein the relay lens is at the distal end of the probe, the relay lens being optically arranged relative to the objective lens for allowing scanning microscopy through the optical window by translating a focal plane of the objective lens into a beam to define a focal point of microscopic imaging outside of the based on the movement of the optical guide by the actuator.

17. The method of claim 16, wherein the distal end of the housing includes tapered surfaces that are tapered outwardly, and wherein the distal end includes both the optical window and a further optical window along the tapered surfaces.

18. The method of claim 16, wherein the relay lens comprises a focusing lens and a mirror, and wherein the wherein the mirror is formed on a partial surface of the focusing lens most distal from the objective lens.

19. The method of claim 16, wherein the relay lens comprises a focusing lens and a mirror, and wherein an optical light path from the objective lens to the optical window passes through a first portion of the focusing lens towards the mirror and passes through the optical window from the mirror and a second portion of the focusing lens.

* * * * *